(12) United States Patent
Payne

(10) Patent No.: US 7,019,180 B2
(45) Date of Patent: Mar. 28, 2006

(54) METHOD OF PURIFYING PHENOL

(75) Inventor: Larry Wayne Payne, Houston, TX (US)

(73) Assignee: Shell Oil Company, Houston, TX (US)

( * ) Notice: Subject to any disclaimer, the term of this patent is extended or adjusted under 35 U.S.C. 154(b) by 165 days.

(21) Appl. No.: 10/762,027

(22) Filed: Jan. 21, 2004

(65) Prior Publication Data

US 2004/0158106 A1    Aug. 12, 2004

Related U.S. Application Data

(60) Provisional application No. 60/445,568, filed on Feb. 6, 2003.

(51) Int. Cl.
*C07C 37/68*  (2006.01)
(52) U.S. Cl. .................... 568/754; 568/758
(58) Field of Classification Search ................ 568/754, 568/758
See application file for complete search history.

(56) References Cited

U.S. PATENT DOCUMENTS

| | | | |
|---|---|---|---|
| 2,948,758 A | 8/1960 | Filar | 260/621 |
| 3,029,294 A | 4/1962 | Keeble | 260/621 |
| 3,454,653 A | 7/1969 | Larson | 260/621 |
| 5,264,636 A | 11/1993 | Shirahata et al. | 568/754 |
| 5,414,154 A | 5/1995 | Jenczewski et al. | 568/754 |
| 5,491,268 A * | 2/1996 | Cipullo | 568/758 |
| 5,502,259 A | 3/1996 | Zakoshansky et al. | 568/754 |
| 6,489,519 B1 | 12/2002 | van Barneveld et al. | 568/754 |
| 2003/0163007 A1 | 8/2003 | Dyckman et al. | 568/754 |

FOREIGN PATENT DOCUMENTS

| | | |
|---|---|---|
| EP | 0568817 A2 | 11/1993 |
| EP | 0578194 A2 | 1/1994 |
| FR | 1445829 | 6/1966 |
| GB | 676770 | 8/1952 |
| GB | 777961 | 7/1957 |
| GB | 920864 | 3/1963 |
| GB | 1121595 | 7/1968 |
| JP | 58065234 | 4/1983 |
| JP | 62-114922 | 5/1987 |

OTHER PUBLICATIONS

V. M. Zakoshansky et al., "Purificatioan of Phenol Derived by Cumene Peroxidation," Zeolites, Elsevier Science Publishing, US, vol. 18, No. 4, Apr. 1, 1997), p. 302.
Kirk-Othmer, Ency. Of Chem. Tech., 4th Ed., vol. 18, pp. 592-602. (1991).
International Search Report of Jul. 29, 2004.
Database WPI Section Ch, Week 198344 Derwent Publications Ltd., London, GB; AN 1983-803578 XP002287062 & JP 58 065234 A (Mitsui Petrochem Ind Co Ltd) Apr. 18, 1983.

* cited by examiner

*Primary Examiner*—Michael L. Shippen

(57) ABSTRACT

A method of purifying a phenol stream that contains a concentration of a contaminating compound is provided. The phenol stream is treated or purified by contacting the stream, under suitable process conditions, with a treatment catalyst that has a low silica content but comprises alumina and a Group VIA metal.

27 Claims, 1 Drawing Sheet

METHOD OF PURIFYING PHENOL

Figure 1:
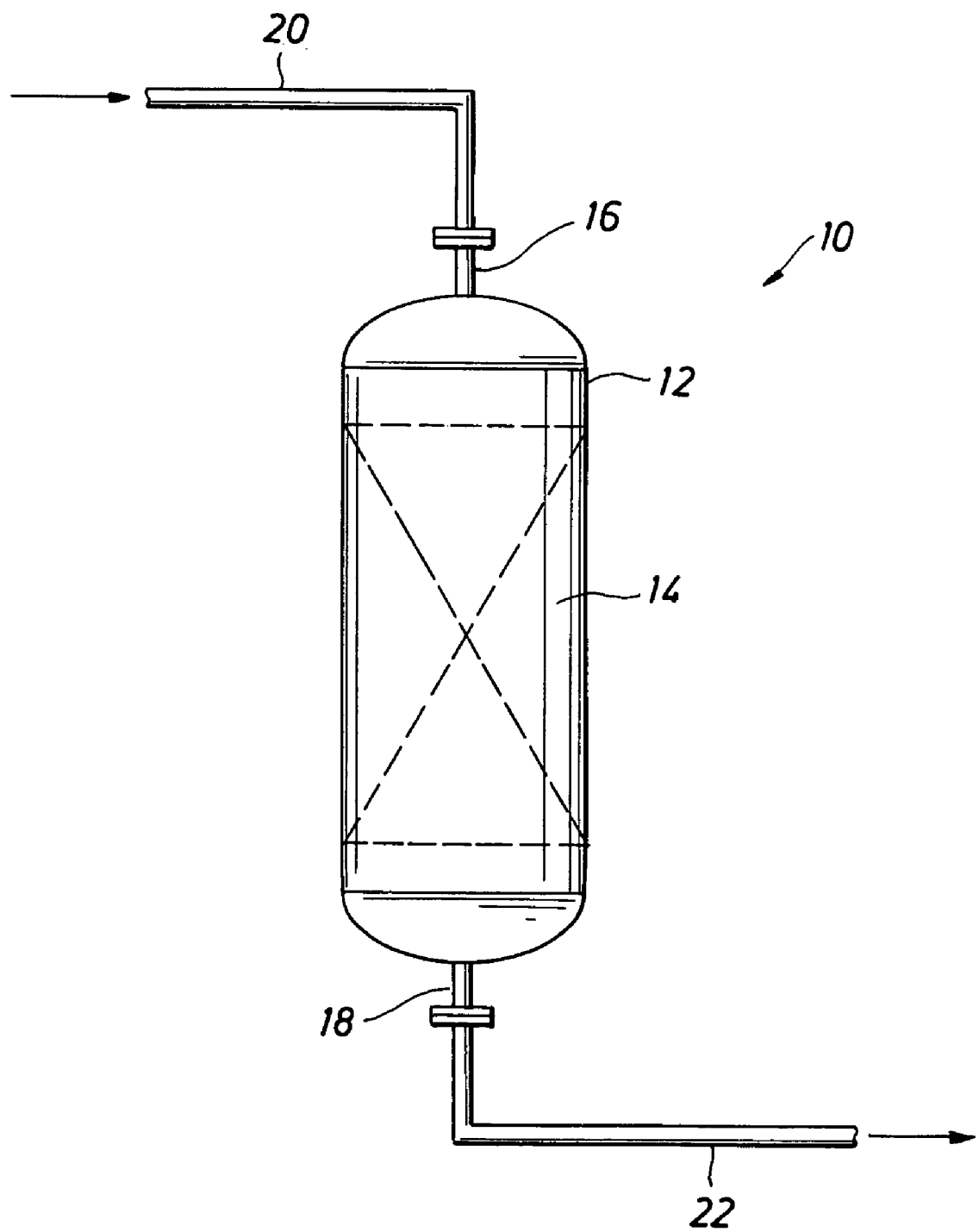

This application claims the benefit of U.S. Provisional Application No. 60/445,568 filed Feb. 6, 2003, the entire disclosure of which is hereby incorporated by reference.

This invention relates to a method of purifying phenol.

One method of making phenol is by oxidizing cumene to cumene hydroperoxide and decomposing the cumene hydroperoxide by a cleavage reaction to yield phenol and acetone reaction products. The phenol produced by this process may contain impurities or product contaminants that are difficult to remove by conventional methods such as by distillation. These impurities are undesirable, because, they cause the formation of color products when the phenol is used in downstream processes involving chlorination or sulphonation of the phenol. Among the contaminants formed during the manufacture of phenol are hydroxyketones.

U.S. Pat. No. 3,454,653 discloses the use of a synthetic silica-alumina catalyst which preferably contains 5% to 30% by weight alumina and 95% to 70% by weight silica. The silica-alumina catalyst may also be modified to contain a group VIA metal, such as chromium, molybdenum or tungsten, in the range of 0.01 to 5% by weight of the catalyst.

U.S. Pat. No. 3,029,294 discloses the use of a number of materials, such as activated alumina, aluminum silicates, ion-exchange resins, mineral acids, strong organic acids, and surface active earths, in the treatment of phenol to convert aliphatic α-hydroxy carbonyl compounds that are present in the phenol to benzofuran.

It is desirable to provide a process for purifying a phenol product that has a concentration of a contaminating compound such as a hydroxyketone.

Other aspects, objects and the several advantages of the invention will become more apparent in light of the following disclosure.

In accordance with the invention, a method is provided for purifying a phenol stream that comprises phenol and a concentration of a contaminating compound. The phenol stream is contacted with a treatment catalyst under conditions suitable for converting a portion of the contaminating compound to another compound to thereby provide a treated phenol stream. The treatment catalyst is a low silica-containing catalyst comprising molybdenum supported on alumina.

FIG. 1 is a schematic diagram illustrating the phenol purification reaction system and process.

The phenol product stream to be treated, or purified, in accordance to the invention can be any phenol-containing material that has a concentration of a contaminant. Thus, the phenol product stream comprises phenol and a concentration of a contaminant with the amount of phenol in the phenol product stream varying from 95 weight percent upwardly to about 100 percent and, preferably, exceeding 98 weight percent and, most preferably, exceeding 99 weight percent of the phenol product stream. The concentration of the contaminant in the phenol product stream is generally a contaminating concentration for the particular contaminant.

While the contaminant component of the phenol product stream may be any compound that imparts undesired properties to the phenol product stream, generally, the contaminant compounds are those compounds yielded as reaction by-products from the production of phenol by the oxidation of cumene followed by the decomposition of the resulting cumene hydroperoxide. One such contaminant of the phenol product stream is an aliphatic hydroxy carbonyl compound, such as, for example, hydroxyketone. The concentration of the contaminant of the phenol product stream to be treated or purified can be in the range of from a contaminating concentration upwardly to about 1 weight percent and, more typically, from 3 parts per million by weight (ppmw) to 10,000 ppmw, or from 5 ppmw to 5000 ppmw. Most typically, the concentration of contaminant will be in the range of from 10 ppmw to 2000 ppmw.

The purified phenol product, or treated phenol product stream, can have a concentration of contaminant that is reduced below the concentration thereof in the phenol product stream that is treated in accordance with the invention. At least a portion, and preferably a major portion, of the contaminant contained in the phenol product stream is either removed from the phenol product stream or converted by reaction to another compound as a reaction product. The reaction product is preferably one that is more easily separable from phenol by conventional distillation methods than is the contaminant. The concentration of contaminant in the purified or treated phenol product is a non-contaminating concentration that is, generally, less than or about 10 ppmw. It is desired, however, for the concentration of contaminant of the purified or treated phenol product stream to be less than or about 5 ppmw, but preferably, less than 3 ppmw. Most preferably, the contaminant concentration in the purified or treated phenol product is less than 1 ppmw or even at a concentration that is not detectable.

The inventive method includes contacting, under suitable contacting conditions, the phenol product stream with an alumina supported, Group VIA metal composition that preferably has a low silica content and, thereafter, yielding or otherwise providing a treated or purified phenol product as described herein. The catalyst is an important aspect of the invention in that it provides for a treated or purified phenol product having a reduced concentration of contaminants; but, moreover, it provides for the conversion of the hydroxyketone contaminants of the phenol product stream without the formation of significant quantities of undesirable benzofurans.

As used in this specification, the term "benzofuran" includes more than the benzene substituted heterocyclic furan compound commonly known as benzofuran but the term also includes, as well, substituted benzofuran compounds including, for example, methyl benzofuran, ethyl benzofuran, dimethyl benzofuran, and diethyl benzofuran.

While benzofuran concentration in the treated phenol will generally depend upon the amount of hydroxyketones in the phenol product stream to be treated, the benzofuran concentration can be a suitably low concentration of less than about 5 ppmw and, preferably, less than 2 ppmw. Most preferably, the benzofuran concentration in the treated phenol is less than 1 ppmw.

The treatment catalyst of the invention comprises a Group VIA metal (Cr, Mo, or W) supported on an inorganic oxide support that has a sufficiently low concentration of silica so as to provide for desired catalytic properties. As used in this specification, any references to the silica concentration as being "low" or "small" or in the "substantial absence" or the like means that the amount of silica in the treatment catalyst composition is at a sufficiently low concentration so as to provide a treatment catalyst having desired catalytic properties for the inventive process. That is, to convert the hydroxyketone contaminants of the phenol product stream without the formation of significant quantities of benzofurans. Such a concentration of silica is less than about 25 weight percent of the total weight of the treatment catalyst composition, but it is better for the amount of silica in the treatment catalyst to be less than about 10 weight percent.

Preferably, the silica content is less than 5 weight percent of the total weight of the treatment catalyst. Most preferred, however, the silica content of the treatment catalyst is less than 3 weight percent. Because of the practical difficulty of having a treatment catalyst with no silica, the lower concentration limit for silica in the treatment catalyst can be 0.1 weight percent, or 0.05 weight percent or even 0.01 weight percent of the total weight of the treatment catalyst.

The preferred inorganic support of the treatment catalyst composition is alumina and the preferred Group VIA metal is molybdenum, which is preferably in the form of an oxide. The treatment catalyst thus has a low concentration of silica, preferably having a substantial absence of silica, and comprises alumina and a Group VIA metal, such as, for example, molybdenum.

The treatment catalyst of the instant invention is prepared by forming a calcined composite comprising a Group VIA metal supported on an inorganic oxide support other than silica or a material having more than a low silica content. The inorganic oxide support comprises a solid usually containing a major proportion of alumina. Such materials are commonly known as refractory oxides and can include synthetic products as well as acid-treated clays. Examples of possible synthetic refractory oxides include alumina, alumina-titania, alumina-magnesia, alumina-zirconia, and thoria. Preferred inorganic oxide supports are alumina refractory oxides, i.e., refractory oxides containing a substantial proportion of alumina, e.g., at least about 90 percent by weight of alumina. Any conventional catalytic grade of alumina including the beta or gamma forms can be used. Generally, the inorganic oxide support has a surface area of at least 10 m$^2$/g and, preferably, the surface area is in the range of from about 25 m$^2$/g to 800 m$^2$/g.

The Group VIA metal can be combined with the inorganic oxide support in any conventional method, such as, for example, by dry mixing, ion-exchange, coprecipitation, impregnation and the like. For example, a 10–100 mesh alumina can be impregnated with an aqueous solution containing a Group VIA metal salt, such as ammonium heptamolybdate or ammonium dimolybdate.

In a preferred embodiment, the treatment catalyst of the invention, comprising alumina and molybdenum oxide, is prepared by impregnating alumina with an aqueous molybdenum impregnation solution. The aqueous molybdenum solution consists of a water-soluble source of molybdenum oxide, such as, for example, ammonium heptamolybdate or ammonium dimolybdate, dissolved in water. Hydrogen peroxide may also be used to aid in solution preparation in some cases. For example, the molybdenum solution can be prepared by adding hydrogen peroxide to the solution in an amount in the range of from about 0.1 to about 1.0 mole of hydrogen peroxide per mole of molybdenum. Optionally, a suitable soluble amine compound such as monoethanolamine, propanolamine or ethylenediamine may be added to the molybdenum solution in order to aid in stabilization of the solution.

Following impregnation, the resulting material is dried and calcined. Drying is accomplished by conventional means. It may be carried out by forced draft drying, vacuum drying, air drying or similar means. Drying temperatures are not critical and depend upon the particular means utilized for drying. Drying temperatures will typically range from about 50° C. to about 150° C.

After drying, the material is calcined to produce the finished treatment catalyst. The material may be calcined in an oxidizing or neutral atmosphere, although air is preferred. However, if binders and/or lubricants are used, the material is heated in an oxygen-containing atmosphere, preferably air, in order to burn out the binders and lubricants. Calcining temperatures will typically range from about 300° C. to about 600° C. Burn-out temperatures will depend on the concentration of oxygen in the burn-out atmosphere as well as the burn-out time involved. Typically, burn-out temperatures will range from about 300° C. to about 600° C. Drying, calcining and burn-out may be combined in one or two steps. Most frequently the calcining and/or burn-out steps are combined using an oxygen-containing atmosphere.

The treatment catalyst typically contains from about 1 percent by weight to about 18 percent by weight, preferably from about 5 percent by weight to about 15 percent by weight, and more preferably from about 6 percent by weight to about 12 percent by weight Group VIA metal.

The process conditions under which the phenol product stream is contacted with the treatment catalyst will vary depending upon the particular contaminant contained in the phenol product stream and on such factors as the contaminant concentration and desired amount of removal. A particularly advantageous feature of the inventive method is that hydroxyketone can be efficiently removed from the phenol product stream using modest process conditions and without producing large amounts of undesirable benzofurans. The contacting temperature can be in the range of from about 50° C. to about 250° C., preferably, from about 90° C. to 230° C. and most preferably, from 100° C. to 210° C.

While it is not a necessary feature of the invention for the phenol product stream to be in the liquid form when contacted with the treatment catalyst, it can be desirable for it to be substantially in the liquid phase. Thus, the contacting pressure can be such that the phenol product stream is substantially liquid and upwardly to about 100 psig. Preferably, the contacting pressure is in the range of from about 10 psig to about 60 psig.

The phenol product stream is contacted with the treatment catalyst by any suitable manner known in the art; but, preferably, the contacting occurs within a reaction zone. The contacting can be as a batch process step or, preferably, as a continuous process step. In the latter operation, a solid bed of treatment catalyst, or a moving bed of treatment catalyst, or a fluidized bed of treatment catalyst can be employed. The contacting step, however, preferably is carried out within a reactor vessel which defines a reaction zone and contains a fixed bed of the treatment catalyst. The reactor vessel, thus, provides means for contacting the phenol product stream with the treatment catalyst under such suitable contacting conditions as, for example, herein described, and for yielding a treated phenol product stream.

The flow rate at which the phenol product stream is charged to the reaction zone is such as to provide a weight hourly space velocity ("WHSV") in the range of from greater than zero to about 1000 hour$^{-1}$. The term "weight hourly space velocity," as used herein, shall mean the numerical ratio of the rate at which the phenol product stream is charged to the reaction zone in pounds per hour divided by the pounds of treatment catalyst contained in the reaction zone to which the phenol product stream is charged. The preferred WHSV of the phenol product stream to the reaction zone can be in the range of from about 0.1 hour$^{-1}$ to about a 250 hour$^{-1}$, preferably, from 0.2 hour$^{-1}$ to 100 hours$^{-1}$, and most preferably, from 0.25 hour$^{-1}$ to 25 hours$^{-1}$.

Now referring to FIG. 1 is a schematic representation of the phenol purification reaction system 10 which includes Reactor 12. Reactor 12 defines a reaction zone that contains a treatment catalyst 14. Reactor 12 is equipped with an inlet 16 and an outlet 18 and provides means for contacting a phenol stream, having a contaminating concentration of hydroxyketone, with treatment catalyst 14 under such suitable contacting conditions as to convert a portion of the hydroxyketone to another compound. The phenol stream is introduced into the reaction zone defined by reactor 12 by way of conduit 20 which is operably connected to inlet 16 so as to provide fluid flow communication with the reaction zone. A purified phenol stream is yielded as a reactor effluent through outlet 18 and conduit 22. Conduit 22 is operably connected to outlet 18 so as to provide for fluid flow communication with the reaction zone.

The following examples are intended to illustrate the present invention and are not intended to unduly limit the scope of the invention.

EXAMPLES

Examples 1–4 describe the experimental procedure used to measure the effectiveness of a low silica content alumina material, especially when such a material is used as a support in combination with molybdenum, in treating a phenol product that contains a contaminating concentration of hydroxyketones. These Examples show that alumina having a low silica content can be effectively used to convert the hydroxyketones contained in the phenol product without an excess production of benzofuran by-products.

In the following Examples 1–4 a pure, anhydrous phenol was used which was collected from a side-draw product stream of a phenol distillation column of a commercial process for manufacturing phenol from cumene. Feeds for each of the examples were prepared by adding small amounts of hydroxyketone impurities using available reagents. The phenol feed was then contacted in the liquid phase by stirring with a catalyst in the amount of 2 percent based on phenol weight for a period of time and at temperatures in the range of 50–150° C. The reaction product mixture was then cooled, filtered, and analyzed by gas chromatography for the individual hydroxyketones and the corresponding benzofuran derivatives. The alumina used for the catalyst contained less than 3 weight percent silica.

Example 1

8% Mo on Alumina γ-Alumina Containing 1–2% Dispersed Silica

A feed containing 990 ppm hydroacetone (HA or acetol), 520 ppm of 1-hydroxy-2-butanone (1HB), and 490 ppm of 3-hydroxy-2-butanone (3HB or acetoin), was prepared from pure phenol and contacted for 2 hours at 145° C. with an alumina catalyst containing approximately 8 percent molybdenum. The catalyst was previously activated and dried. Conversion of hydroxyketones averaged 98, 98, and 100 percent for HA, 1HB, and 3HB, respectively, for three separate experiments. Approximately 6 percent of the HA was converted to 2-methyl benzofuran, 3 percent of the 1-HB was converted to 2-ethyl benzofuran, and 3 percent of 3-HB was converted to 1,3-dimethyl benzofuran.

Example 2

4% Mo on γ-Alumina Containing 1-2% Dispersed Silica

A feed containing 990 ppm hydroacetone (HA or acetol), 520 ppm of 1-hydroxy-2-butanone (1HB), and 490 ppm 3-hydroxy-2-butanone (3HB or acetoin), was prepared from pure phenol and contacted for 2 hours at 145° C. with an alumina catalyst containing approximately 4 percent molybdenum. The catalyst was previously activated and dried. Conversion of hydroxyketones averaged 84, 87 and 98 percent for HA, 1HB, and 3HB, respectively, for three separate experiments. The corresponding benzofuran selectivities averaged approximately 6, 3, and 2.5 percent.

Example 3

Alumina Only

A feed containing 990 ppm HA, 520 ppm of 1HB, and 490 ppm of 3HB was prepared from pure phenol and contacted for 2 hours at 145° C. with an alumina catalyst containing no molybdenum and which had been previously activated and dried. Conversion of hydroxyketones were 18, 15, and 8 percent for HA, 1HB, and 3HB, respectively. The corresponding benzofuran selectivities were approximately 2, 0.5, and 2 percent.

Example 4

Blank—Heat But No Catalyst

A feed containing 990 ppm HA, 520 ppm of 1HB and 490 ppm of 3HB was prepared from pure phenol and heated for 2 hours at 145° C. without addition of a catalyst. Conversion of hydroxyketones averaged 5, 5, and 7 percent for HA, 1HB, and 3HB, respectively, for three separate experiments. The corresponding benzofuran selectivities averaged approximately 3, 0.1, and 3 percent.

The following table summarizes the results from the above tests.

TABLE I

Conversion of the Hydroxyketone Contained in a Phenol Product Using Different Catalysts

| | % Conversion of hydroxyketones | | | % Selectivity to benzofuran | | |
|---|---|---|---|---|---|---|
| | HA | 1HB | 3HB | HA | 1HB | 3HB |
| 8% Mo on alumina | 98 | 98 | 100 | 6 | 3 | 3 |
| 4% Mo on alumina | 84 | 87 | 98 | 6 | 3 | 2.5 |
| alumina only | 18 | 15 | 8 | 2 | 0.5 | 2 |
| no catalyst | 5 | 5 | 7 | 3 | 0.1 | 3 |

The conversion data presented in Table I above show the advantages from using either a low silica content alumina or molybdenum supported on a low silica content alumina in the treatment of a phenol product that contains a concentration of hydroxyketone when compared to the use of no treatment catalyst. As can be observed, the conversion of hydroxyketones using the catalyst was better than using no catalyst. Also, the selectivity to benzofuran was very low and, in most cases, 3 percent or less. The molybdenum/alumina catalysts provided significantly better conversion of hydroxyketones than the alumina only catalyst, and the molybdenum/alumina catalysts still provided for low selectivity to benzofuran.

While this invention has been described in terms of the presently preferred embodiment, reasonable variation and modifications are possible by those skilled in the art. Such variations and modifications are within the scope of the described invention and appended claims.

That which is claimed is:

1. A method, comprising:
   purifying a phenol product, comprising phenol and a contaminating concentration of an hydroxyketone, by contacting, under suitable contacting conditions, said phenol product with a treatment catalyst consisting essentially of alumina and a Group VIA metal.

2. The method of claim 1 wherein the amount of phenol in said phenol product is in the range of from 95 weight percent upwardly to about 100 weight percent.

3. The method of claim 2 wherein said contacting conditions include a contacting temperature in the range of from about 50° C. to about 250° C. and a contacting pressure upwardly to about 100 psig.

4. The method of claim 3 wherein said treatment catalyst has a concentration of silica less than about 25 weight percent of the treatment catalyst.

5. The method of claim 4 wherein said Group VIA metal is molybdenum which is present in the treatment catalyst in an amount in the range of from about 1 percent by weight to about 18 percent by weight of the treatment catalyst.

6. The method of claim 5 further comprising yielding a treated phenol product having a concentration of said hydroxyketone that is reduced below the concentration thereof in said phenol product.

7. The method of claim 6 wherein said concentration of said hydroxyketone in said treated phenol product is less than about 3 ppmw.

8. The method of claim 1 wherein said treatment catalyst has a concentration of silica less than about 25 weight percent of the treatment catalyst.

9. The method of claim 8 wherein said Group VIA metal is molybdenum which is present in the treatment catalyst in an amount in the range of from about 1 percent by weight to about 18 percent by weight of the treatment catalyst.

10. The method of claim 8 wherein said contacting conditions include a contacting temperature in the range of from about 50° C. to about 250° C. and a contacting pressure upwardly to about 100 psig.

11. A method, comprising:
    contacting under suitable reaction conditions a phenol stream, comprising phenol and hydroxyketone, with a treatment catalyst having a low silica content and further comprising alumina and a Group VIA metal.

12. The method of claim 11 wherein said reaction conditions include a contacting temperature in the range of from about 50° C. to 250° C. and a contacting pressure upwardly to about 100 psig.

13. The method of claim 12 wherein the amount of phenol in said phenol stream is in the range of from 95 weight percent upwardly to about 100 weight percent.

14. The method of claim 13 wherein the amount of silica in said treatment catalyst is in the range of less than about 25 weight percent of the total weight of the treatment catalyst and the amount of Group VIA metal in said treatment catalyst is in the range of from about 1 weight percent to about 18 weight percent of the treatment catalyst.

15. The method of claim 14 further comprising yielding a treated phenol product having less than about 3 ppmw hydroxyketone.

16. The method of claim 11 wherein said treatment catalyst has a concentration of silica less than about 25 weight percent of the treatment catalyst.

17. The method of claim 16 wherein said Group VIA metal is molybdenum which is present in the treatment catalyst in an amount in the range of from about 1 percent by weight to about 18 percent by weight of the treatment catalyst.

18. The method of claim 16 wherein said contacting conditions include a contacting temperature in the range of from about 50° C. to about 250° C. and a contacting pressure upwardly to about 100 psig.

19. A method of purifying a phenol stream comprising phenol and hydroxyketone, said method comprises:
    providing a reactor having an inlet and an outlet and which defines a reaction zone containing a low silica-containing treatment catalyst comprising alumina and a Group VIA metal;
    introducing said phenol stream into said reaction zone through said inlet;
    operating said reaction zone under suitable reaction conditions to convert at least a portion of said hydroxyketone in said phenol stream to another compound; and
    removing a purified phenol stream from said reaction zone as a reactor effluent through said outlet.

20. The method of claim 19 wherein the amount of silica in said low silica-containing treatment catalyst is in the range of less than 25 weight percent of the total weight of said low silica-containing treatment catalyst and the amount of Group VIA metal in said treatment catalyst is in the range of from about 1 weight percent to about 18 weight percent of the total weight of said low silica-containing treatment catalyst.

21. The method of claim 20 wherein the amount of phenol in said phenol stream is in the range exceeding 95 weight percent of the total phenol stream.

22. The method of claim 21 wherein said reaction conditions include a contacting temperature in the range of from about 50° C. to about 250° C. and a contacting pressure upwardly to about 100 psig.

23. The method of claim 22 wherein the concentration of hydroxyketone in said reactor effluent is less than about 3 ppmw.

24. The method of claim 19 wherein said reaction conditions include a contacting temperature in the range of from about 50° C. to about 250° C. and a contacting pressure upwardly to about 100 psig.

25. The method of claim 20 wherein said treatment catalyst has a concentration of silica less than about 25 weight percent of the treatment catalyst.

26. The method of claim 25 wherein said Group VIA metal is molybdenum which is present in the treatment catalyst in an amount in the range of from about 1 percent by weight to about 18 percent by weight of the treatment catalyst.

27. The method of claim 25 wherein said contacting conditions include a contacting temperature in the range of from about 50° C. to about 250° C. and a contacting pressure upwardly to about 100 psig.

* * * * *